United States Patent [19]
Baumbach et al.

[11] Patent Number: 5,807,550
[45] Date of Patent: Sep. 15, 1998

[54] ANTIBODIES SPECIFICALLY RECOGNIZING SOMATOTROPIN BINDING PROTEINS

[75] Inventors: William Robert Baumbach, Hopewell; Bosco Shang Wang, Cranbury; Homayoun Sadeghi; John Steele Logan, both of Robbinsville; Ian C. Hart, Pennington, all of N.J.

[73] Assignee: American Cyanamid Company, Madison, N.J.

[21] Appl. No.: 461,902

[22] Filed: Jun. 5, 1995

Related U.S. Application Data

[62] Division of Ser. No. 473,086, Jan. 31, 1990, Pat. No. 5,439,795.

[51] Int. Cl.⁶ .................. A61K 39/00; A61K 39/395; G01N 33/53; C07K 16/00
[52] U.S. Cl. .................. 424/145.1; 424/198.1; 530/388.24; 530/387.9; 435/7.1; 435/172.2; 435/331; 435/332; 435/336
[58] Field of Search .................. 435/7.1, 240, 240.47, 435/172.2, 331, 332, 336; 530/387.9, 388, 388.24; 424/198.1

[56] References Cited

PUBLICATIONS

Lerner, Nature 299:592–596, 1982.

Baumbach et al., Genes and Development 3(8):1199–1205, 1989.

Smith et al., Molecular Endocrinology 3(6):984–990, 1989.

Sevier et al., Clin. Chem. 27(11) :1979–1806, 1981.

*Primary Examiner*—Lila Feisee
*Assistant Examiner*—Geetha P. Bansal
*Attorney, Agent, or Firm*—Anne M. Rosenblum

[57] ABSTRACT

The present invention is directed to antibodies, in particular monoclonal antibodies, which specifically bind to somatotropin binding proteins of animals, but not with the corresponding somatotropin receptors. The antibodies may be used alone to enhance the growth of animals, or may be used together with somatotropin to potentiate the effect of somatotropin in animals. The antibodies may also be used to assay the level of somatotropin binding protein of animals.

8 Claims, 5 Drawing Sheets

ANTIBODIES SPECIFICALLY RECOGNIZING SOMATOTROPIN BINDING PROTEINS

This is a divisional of application Ser. No. 07/473,086 now U.S. Pat. No. 5,439,795, filed on Jan. 31, 1990.

FIELD OF THE INVENTION

The present invention is directed to antibodies, in particular monoclonal antibodies, which specifically recognize somatotropin binding proteins. Due to the unique peptide sequences of the antigens to which the monoclonal antibodies are raised, these monoclonal antibodies are highly specific to somatotropin binding proteins but not to somatotropin receptors. These monoclonal antibodies can be used to modify and enhance the hormonal effects of somatotropin in animals.

BACKGROUND OF THE INVENTION

Somatotropin is a polypeptide secreted by the anterior pituitary in animals and acts through specific cell surface receptors located primarily in the liver (Bibliography 1). Recently, a protein which binds somatotropin with high affinity has been identified in serum (2,3,4). This serum somatotropin binding protein closely resembles the molecules of the somatotropin receptor present on the surface of target cells and a large body of evidence has suggested the colinearity and identity between the extracellular domain of the somatotropin receptor and the somatotropin binding protein (5,6,7,8,9,10,11). Monoclonal antibodies have been raised to the somatotropin receptor which cross-react with somatotropin binding protein (12). It has also been proposed that the somatotropin binding protein is a product of proteolytic cleavage of the somatotropin receptor (9,11,13).

Recently, two species of somatotropin-related mRNA's in rats have been identified and cDNA cloned (14). One mRNA encodes a membrane bound somatotropin receptor and the other encodes the somatotropin binding protein which is a secreted soluble protein identical to the extracellular region, but lacking the transmembrane and intracellular domains of the somatotropin receptor. This extracellular region is replaced by an alternative splicing mechanism with a 17 amino acid hydrophilic segment followed by a unique 3' untranslated region. Thus, the somatotropin binding protein in rat has a unique carboxyl terminus which is absent in the somatotropin receptor. A similar molecular structure has also been reported with mouse somatotropin binding protein (15).

SUMMARY OF THE INVENTION

The present invention relates to antibodies, in particular monoclonal antibodies that react with somatotropin binding proteins. Unlike other monoclonal antibodies that react with somatotropin binding proteins, those comprising this invention do not also react with the somatotropin receptor. This is because they are produced against a unique antigen which is found in the rat and other animal somatotropin binding proteins, but not in any somatotropin receptor. These antibodies are useful in distinguishing somatotropin binding proteins from somatotropin receptors, and in altering the serum levels or other qualities of serum somatotropin binding proteins in animals to improve their growth characteristics.

Figure 1:
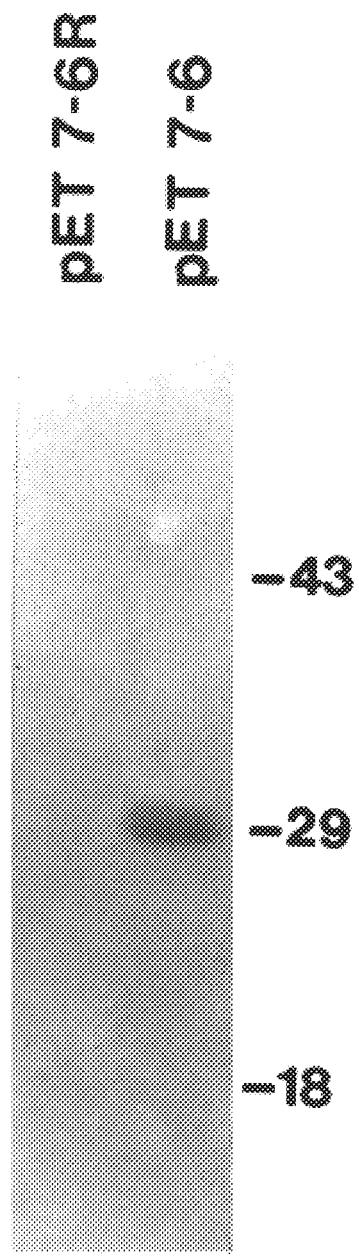
FIG. 1 depicts the specific interaction of GHBP-4.3 monoclonal antibody with rat somatotropin binding protein. Cell extracts from E. coli bacteria with expression plasmid pET-7.6 m, which directs the synthesis of rat somatotropin binding protein, were electrophoresed on 15% polyacrylamide gel, transferred onto filter paper and probed with GHBP-4.3 monoclonal antibody and later with $^{125}$I-protein A (Staph A bacterial protein which binds IgG) and autoradiographed. Lane 2 contains proteins from E. coli cells which express rat somatotropin binding protein. Lane 1 contains E. coli extract with the expression plasmid with rat somatotropin binding protein sequences in reverse orientation. As shown, bacteria with rat somatotropin binding protein sequences in correct orientation can express a protein recognized by GHBP-4.3 monoclonal antibody which migrates at 30 Kd. Molecular weight markers are shown on the right (43 Kd—ovalbumin; 29 Kd—carbonic anhydrase; 18 Kd—beta-lactoglobulin).

4A: Three week old Balb/C mice were injected with one mg of GHBP-4.3 monoclonal antibody (Δ–Δ) or kept as untreated control (●–●) and their weight gain was monitored for two weeks. Each point represents the average weight gain of 10 mice. Data from control mouse IgG are not included in FIG. 4A, but are presented in Exanple 9 below.

4B: Three week old mice were treated with 100 µg GHBP-4.3 monoclonal antibody+10 µg somatotropin (●–●) or 100 µg control mouse IgG (Δ–Δ) or 10 µg somatotropin alone (○–○) and their weight gain was monitored for 35 days. Each point represents the average weight gain of four mice.

DETAILED DESCRIPTION OF THE INVENTION

This invention is directed to the preparation of antibodies, in particular monoclonal antibodies to a unique region of the somatotropin binding protein and their use to enhance the growth of animals and to assay the level of somatotropin binding protein. As a preliminary step, a peptide corresponding to this unique region is synthesized as follows:

Sequence analysis of cDNA clones representing the rat somatotropin receptor and the rat serum somatotropin binding protein revealed that the following nucleotide sequence was transcribed to make mRNA of somatotropin binding protein but not somatotropin receptor: GGA CCC AAG TTC AAT TCC CAG CAC CCA CAT CAA GAG ATT GAC AAC CAC CTG TAA. This DNA sequence translated as Gly-Pro-Lys-Phe-Asn-Ser-Gln-His-Pro-His-Gln-Glu-Ile-Asp-Asn-His-Leu, followed by a stop codon, indicating that it formed the carboxyl terminus of the somatotropin binding protein. Using a solid-phase peptide synthesis procedure (the Fmoc polyamide method), this unique region was synthesized with the addition at position 1 of Cys residue, which was included for the purpose of coupling the peptide to an antigenic carrier protein.

The 18 amino acid peptide is then purified by suitable means such as high performance liquid chromatography (HPLC). The purity of the peptide is demonstrated by amino acid composition analysis.

A comparable procedure may be used to generate an 18 amino acid peptide which corresponds to the unique carboxyl terminal region of the mouse somatotropin binding protein plus a Cys residue. The mouse region has the following sequence: Gly-Thr-Lys-Ser-Asn-Ser-Gln-His-Pro-His-Gln-Glu-Ile-Asp-Asn-His-Leu (15).

In order to enhance the formation of antibodies, a peptide of this invention preferably is linked to a macromolecule which functions as a carrier for the peptide. For example, the peptide may be conjugated to a protein such as keyhole limpet haemocyanin (KLH). Other carriers within the scope of this invention include those known in the art such as human and bovine serum albumins, myoglobins, β-galactosidase, penicillinase and bacterial toxoids. The carriers may also be synthetic molecules such as multi-poly-DL-alanyl-poly-L-lysine and poly-L-lysine.

Monoclonal antibodies are generated by immunizing animals with a peptide of this invention, either alone or in conjugated form. The peptide may be administered by conventional routes such as subcutaneous injection, intramuscular injection and intravenous flow, as well as transdermal and oral administration. It is preferred to administer the peptide (or its conjugate) in association with a carrier containing an adjuvant, such as Freund's complete adjuvant. It is particularly preferred to use a dosage regimen where an initial administration of the peptide is followed by one or more booster administrations of the same peptide at regular time intervals.

This invention is also directed to monoclonal antibodies to peptides having amino acid sequences which are antigenically equivalent to those described above for the 18 amino acid peptide. Such peptides may be said to be antigenically equivalent to that peptide by having amino acid sequences homologous to the unique carboxyl terminal region if their amino acid sequences differ only by minor deletions from or conservative substitutions to the amino acid sequence of the 18 amino acid peptide so that the tertiary configurations of the peptides are substantially unchanged from those of that 18 amino acid peptide and antibodies can be generated to those peptides.

Further steps for preparing monoclonal antibodies include removing the spleens of the animals immunized with the peptide, preparing suspensions of lymphocytes, fusing these lymphocytes to mouse myeloma cells, culturing the cells and collecting supernatants of surviving hybridomas for antibody screening by solid-phase enzyme-linked immunosorbent assay (ELISA). Those hybridomas which produce desired antibodies are further subcloned and injected in mice.

Samples of the hybridoma designated GHBP-4.3 have been deposited on Dec. 15, 1989 with the American Type Culture Collection 12301 Parklawn Drive, Rockville, Md. 20852 U.S.A. and have been assigned accession number ATCC HB 10310.

Monoclonal antibodies are then purified as follows: Ascites are collected from the peritoneal cavities of mice and immunoglobulin (Ig) is purified either by ammonium sulfate precipitation or by a Protein A affinity column on a fast protein liquid chromatography (FPLC) system. Samples of Ig so purified contain the desired monoclonal antibodies, which can be identified in an assay against antigens using ELISA.

The ability of such monoclonal antibodies to bind to somatotropin binding protein is tested by means of an assay such as a Western blot assay. As shown in FIG. 1, a monoclonal antibody specifically recognizes somatotropin binding protein (Lane 2), but does not interact with any protein of E. coli which contains an expression plasmid in which the somatotropin binding protein sequence is in reverse orientation (such a strain is unable to express the somatotropin binding protein) (Lane 1).

Figure 2:
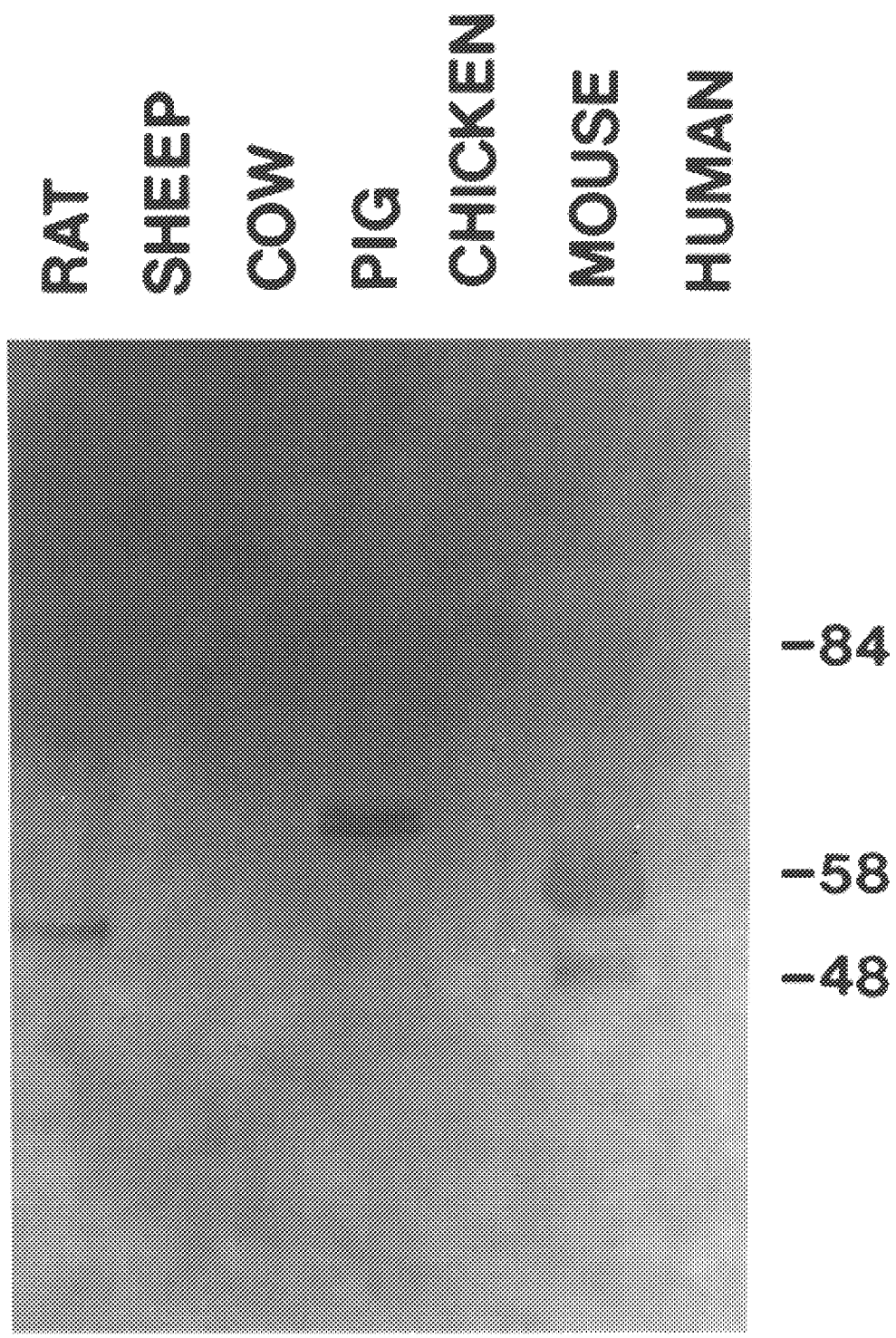
FIG. 2 depicts the specific interaction of GHBP-4.3 monoclonal antibody with somatotropin binding protein in blood. One µl of plasma from each animal shown was electrophoresed on 15% polyacrylamide gel and blotted on Immobilon-P filter paper (Millipore). The blot was probed with GHBP-4.3 monoclonal antibody and later alkaline phosphatase-labelled anti-mouse secondary antibody. The Western Blot was then developed for alkaline phosphatase activity. As shown, GHBP-4.3 monoclonal antibody recognizes a somatotropin binding protein in the rat (Lane 1), pig (Lane 4) and mouse (Lane 6) plasma. The presence of mouse immunoglobulin in plasma causes an extra band of 55 Kd to interact with immunoglobulin secondary antibody. Molecular weight markers are shown on the right (84 Kd—fructose-6-phosphatase; 58 Kd—pyruvate kinase; 48 Kd—fumarase).

In another aspect of this invention, a monoclonal antibody may be used to identify somatotropin binding protein in a sample of blood plasma. The plasma is electrophoresed on a gel such as polyacrylamide, the proteins thus separated are electroblotted and are then incubated with a monoclonal antibody of this invention. The blots are exposed to a labelled anti-mouse antibody and then developed. This assay may be used to demonstrate that the antibody reacts with somatotropin binding protein. Results for the rat are shown in FIG. 2 (Lane 1).

The cross-reactivity of a monoclonal antibody with the somatotropin binding protein of various species has also been tested by subjecting the EDTA-treated plasma of various animals to SDS-PAGE and Western blotting using the procedure set forth above for rat plasma. As shown in FIG. 2, the monoclonal antibody reacts with rat, mouse and pig somatotropin binding protein, but not with the cow, sheep, chicken and human binding protein. This result suggests that a homologous carboxy terminal domain exists in the rat, mouse and pig somatotropin binding protein.

The monoclonal antibodies which bind to the somatotropin binding protein do not react with the somatotropin receptor, because the receptor protein does not contain the unique carboxy terminal region of the binding protein from which the monoclonal antibodies were raised.

There are several ways that GHBP-4.3 monoclonal antibody can be used to measure the level of somatotropin binding protein in serum. In one procedure, sodium dodecyl sulfate polyacrylamide gel electrophoresis is utilized; 2-mercaptoethanol may be used as a denaturant. A sample of a known level of somatotropin binding protein from bacteria is used as a control. The test sample is a known volume of serum. The electrophoresed gel is subjected to Western blotting, first with GHBP-4.3 monoclonal antibody and then with radioactive anti-mouse immunoglobulin as a secondary antibody. The intensity of the radioactive signal from serum is compared to that of the level for the known amount of bacterial somatotropin binding protein, thus estimating the level of binding protein in serum.

In another procedure, a radioimmunoassay/immunoprecipitation technique is utilized. Somatotropin binding protein from bacteria is radiolabelled with, for example, $^{125}$I. The radiolabelled somatotropin binding protein can form an immunocomplex with GHBP-4.3 monoclonal antibody. The labelled protein is used as a tracer ligand. The labelled ligand can be displaced by a known level of unlabelled ligand. This displacement is monitored, resulting in a competition curve which is used as a standard curve for the radioimmunoassay. The level of somatotropin binding protein in serum is ascertained by using a known volume of serum as an unlabelled competitor and referring the level of displacement to the standard curve to measure the amount of somatotropin binding protein.

Figure 4A:
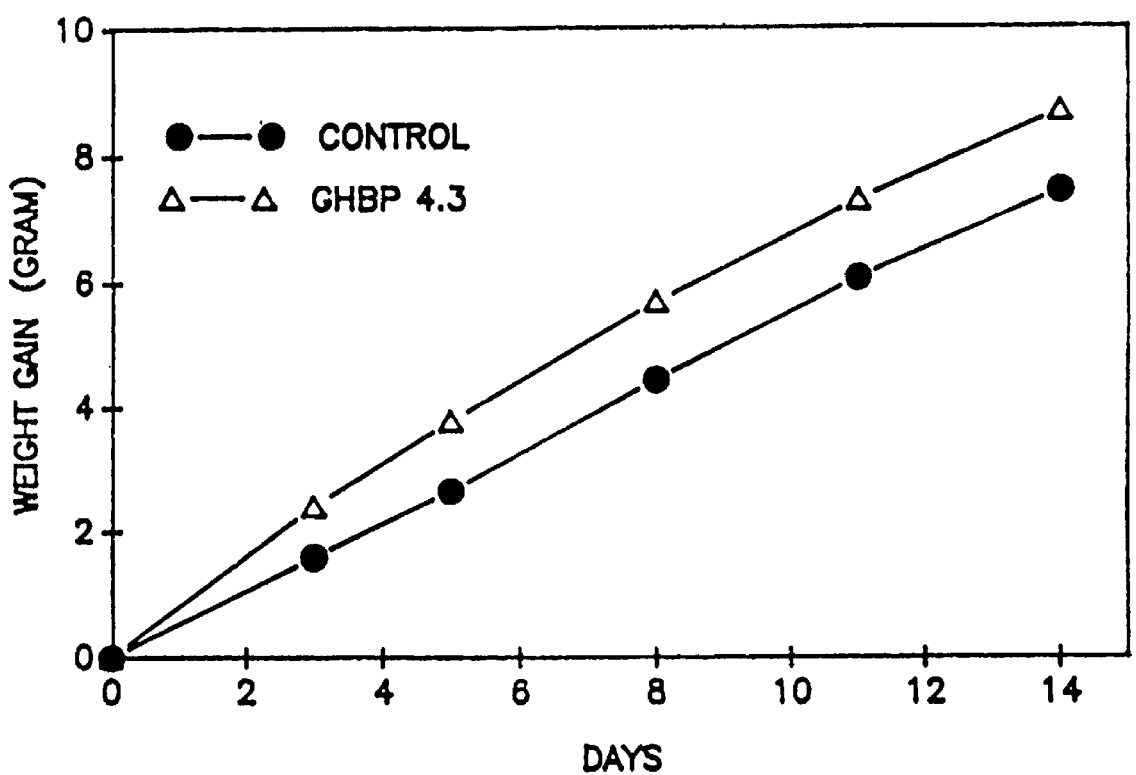
FIGS. 4A and 4B depict the effect of GHBP-4.3 monoclonal antibody on the growth of Balb/C mice in two separate experiments.

In another aspect of this invention, antibodies specifically recognizing somatotropin binding protein are used to enhance the growth of an animal. One or more such antibodies may be used. All, some or none of such antibodies may be monoclonal antibodies. The selection of antibodies to be used is within the scope of persons skilled in the art. FIG. 4A presents the results of such an experiment. Mice treated with a monoclonal antibody of this invention grow more quickly than those which are not so treated.

Figure 4B:
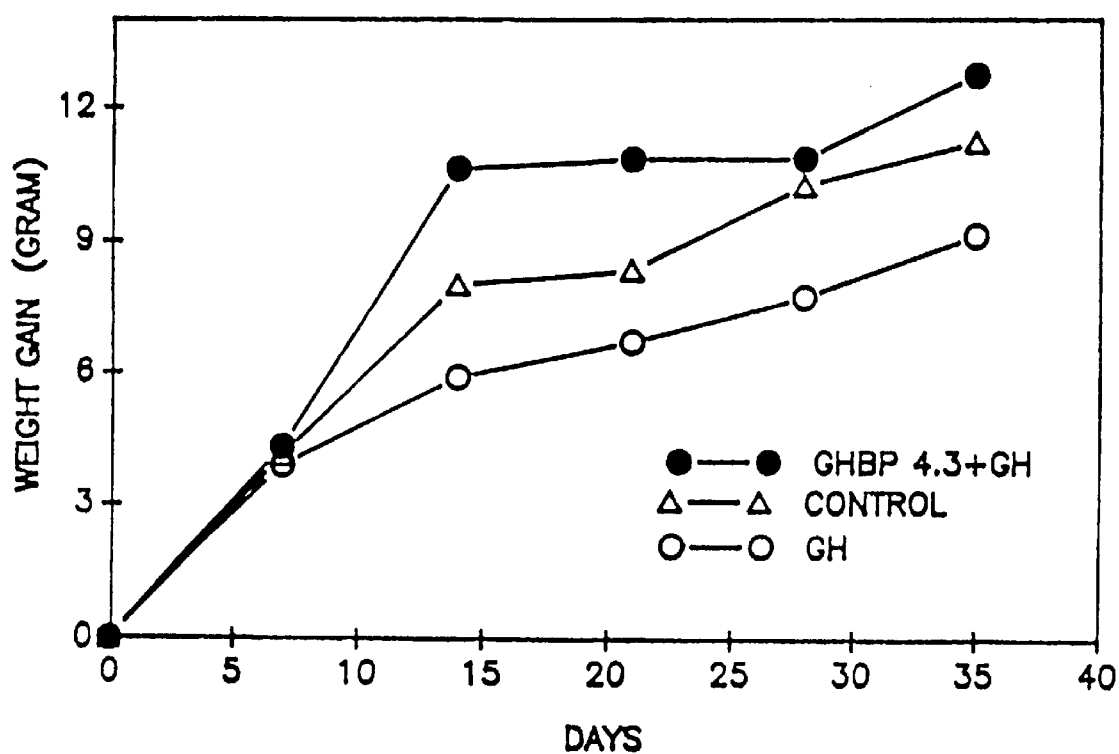

In yet another aspect of this invention, the novel antibodies described herein are administered with somatotropin to potentiate the effect of somatotropin in an animal. Again, one or more such antibodies may be used and all, some or none of the antibodies may be monoclonal. FIG. 4B presents the results of such an experiment. Mice treated with a monoclonal antibody of this invention together with mouse somatotropin gain weight at a faster rate than mice treated with somatotropin alone.

In order that this invention may be better understood, the following examples are set forth. The examples are for the purpose of illustration only and are not to be construed as limiting the scope of the invention.

EXAMPLE 1

Preparation of a Synthetic Peptide Representing the Unique Region of the Somatotropin Binding Protein An 18 amino acid peptide corresponding to the unique carboxy terminal region of the somatotropin binding protein with the addition at position 1 of Cys residue (included for the purpose of coupling the peptide to an antigenic carrier protein) is produced with the following sequence: Cys-Gly-Pro-Lys-Phe-Asn-Ser-Gln-His-Pro-His-Gln-Glu-Ile-Asp-Asn-His-Leu using a solid-phase peptide synthesis procedure (the Fmoc polyamide method). The peptide preparation is analyzed for purity on a Vydac $C_{18}$ (4.6 mm×25 cm) HPLC column, using a linear gradient over 30 minutes of 10–50% 0.1% TFA/CH$_3$CN and 90–50% 0.1% TFA/H$_2$O with a flow rate of 1.5 cm$^3$/minute. Detection is by UV at 230 nm. Amino acid analysis is performed by acid hydrolysis followed by thin layer chromatography to give the results shown in Table I:

TABLE I

Amino Acid Analysis Of Synthetic Peptide

| Amino Acid | Number of Residues | |
|---|---|---|
| | Actual | Calculated |
| Asparagine & Aspartic acid | 2.90 | 3 |
| Aspartic acid | | |
| Cysteine | * | 1 |
| Glutamine & Glutamic acid | 3.10 | 3 |
| Glycine | 1.00 | 1 |
| Histidine | 2.77 | 3 |
| Isoleucine | 1.07 | 1 |
| Leucine | 1.06 | 1 |
| Lysine | 0.95 | 1 |
| Phenylalanine | 0.98 | 1 |
| Proline | 3.30* | 2 |
| Serine | 0.84 | 1 |
| Total | 17.97 | 18 |

*Cysteine degrades on acid hydrolysis to give a product which co-elutes with proline.

Fast atom bombardment mass spectrometry provides a molecular weight determination (positive ion spectrum gives M+H$^+$ at m/z 2100) and sequence confirmation.

EXAMPLE 2

Conjugation of the Synthetic Peptide with a Highly Antigenic Carrier Protein

The synthetic peptide of Example 1 is conjugated with KLH via the thiol group of the cysteine residue at position 1 of the peptide. Ten milligrams of the pure synthetic peptide are coupled to 8 mg of KLH using m-maleimidobenzoic acid N-hydroxysuccinimide ester as a heterobifunctional cross-linking agent to produce N-terminally bound peptide conjugates. The resultant conjugates are dialyzed, lyophilized, and stored at −20° C. prior to use.

EXAMPLE 3

Generation of Monoclonal Antibody to Somatotropin Binding Protein

Balb/C mice, 6 to 10 weeks of age, are purchased from Charles River Breeding Laboratories, Wilmington, Mass. These mice are immunized with 100 μg KLH-peptide conjugate which is emulsified in complete Freund's adjuvant. These animals are boostered with 50 μg of the same antigen every 3 weeks thereafter. Their spleens are removed 3 days after the last boosting and single cell suspensions of lymphocytes are prepared. These lymphocytes are fused with NS-1 mouse myeloma cells (American Type Culture Collection, Rockville, Md.) lacking hypoxanthine phosphoribosyl transferase (HPRT) with 50% polyethylene glycol, suspended in Dulbecco's modified Eagle medium (D-MEM) containing 20% fetal calf serum (FCS) (Gibco), 0.175 μg/ml aminopterin, 13.6 μg/ml hypoxanthine, 3.88 μg/ml thymidine and 50 μg/ml gentamicin (HAT medium), and finally dispensed in 96-well culture plates. After being cultured for 10–14 days, supernatants of the several hundred hybridomas who survived due to the HPRT-positive phenotype of the lymphocytes are collected for antibody screening in a solid-phase ELISA. Fourteen hybridomas designated GHBP-1 to GHBP-14 are determined to produce appropriate antibodies by solid phase ELISA and Western analysis, wherein a bacterial lysate from the strain *E. coli* JM 109 (DE 3)/pET 7-6 m (samples of which have been deposited with the American Type Culture Collection and have been assigned accession number ATCC 68,205) is probed with each monoclonal antibody, and are further subcloned by a limited dilution procedure.

The *E. coli* strain JM 109 (DE3)/pET 7-6 m is generated as follows: *E. coli* bacteria are directed to synthesize rat somatotropin binding protein using the cDNA sequence of somatotropin binding protein in a T7 polymerase expression system. Plasmid pRat 7-6 (ATCC number 67,849) is described in co-pending, commonly-assigned U.S. application Ser. No. 310,725, filed Feb. 17, 1989, and is used to generate plasmid pRat 7-6 m as follows: pRat 7-6 is digested with the restriction enzyme EcoRI and a 0.95 kb fragment containing the serum somatotropin binding protein is isolated. This fragment is ligated into the vector pGEM 3Z(f)+ (Promega Biotech, Wis.) which is digested with EcoRI. The orientation of the fragment is such that the 5' end of the somatotropin binding protein gene adjoins the T7 RNA polymerase promoter (16). The resulting construct, pRat 3Z+7-6, is used for site-directed mutagenesis.

The strain *E. coli* DH5α/pRat 3Z+7-6 is superinfected with the helper phage R408 (Promega Biotech, Wis.), and single stranded DNA is isolated. This DNA represents the negative strand with respect to the serum somatotropin binding protein coding region. An oligonucleotide of the sequence 5'GTCTCCAGCCATATGTTTCCT3' is synthesized and annealed to the single stranded DNA. The second strand is completed using the Klenow fragment of *E. coli* DNA polymerase and T4 DNA ligase. *E. coli* strain DH5α (Bethesda Research Laboratories, Gaithersburg, Md.) is transformed, and the mixture plated on LB-AMP plates. The colonies are transferred to nitrocellulose.

Colony hybridization is performed in 1X Denhardts, 5X SSC and 150 μl/ml tRNA at 37° C. using as a probe the oligonucleotide which is end labeled with $^{32}$P ATP. The filters are washed at 56° C. in 3M tetramethyl ammonium chloride, 50 mM Tris, pH 8, 2 mM EDTA and 0.1% sodium dodecyl sulfate (SDS). Under these conditions, only colonies containing plasmids with the mutated sequence are labelled. Positive colonies are picked, from which plasmid DNA is made which may contain both mutant and wild type molecules. The transformation, hybridization and washing procedures are repeated, and a positive colony is again picked and used to make the purified mutant plasmid pRat 7-6 m.

The plasmid pRat 7-6 m encodes a recombinant rat somatotropin binding protein in which a Nde I restriction site has been engineered at the methionine residue at position 18 of the normal molecule. The 0.9 kb fragment excised by digestion with restriction endonuclease Nde I is ligated into the vector pET3b (17) at the unique Nde I site. Thus, the methionine residue at position 18 serves as the initiation site for translation in this plasmid, which is called pET 7-6 m. The resultant somatotropin binding protein molecule lacks the putative signal sequence of the wild type unprocessed molecule as predicted by Leung et al. (9).

This residue (methionine 18) is not necessarily the first residue of the processed serum somatotropin binding protein found in rats (the initial residue of the processed wild type molecule has been predicted to be the threonine residue at position 25 in rat by Mathews et al. (18) and has been shown by amino-terminal sequencing to be the corresponding threonine 25 residue in mouse by Smith et al. (15). The present molecule nevertheless represents a functionally equivalent species (as evidenced by the use of a cleavage site in human and rabbit after residue 17 (9)), and allows for translation of the present rat somatotropin binding protein in bacteria without the addition of the required initiator methionine residue at a position which does not exist in the wild type molecule.

Transcription of the recombinant rat somatotropin binding protein is driven by a phage T7 gene promoter that signals constitutive transcription by phage T7 RNA polymerase, which is not normally found in *E. coli*. Therefore, an *E. coli* strain, JM 109 (DE 3) (Promega, Inc.), that has a copy of the T7 RNA polymerase gene in a lambda lysogen, is used for expression of the recombinant somatotropin binding protein. This T7 RNA polymerase gene is under the control of an inducible promoter (lacUV5). Thus, expression of the recombinant somatotropin binding protein is induced by the addition of 0.4 mM isopropylthiogalactoside (IPTG) into the medium (19). An additional plasmid, pLysS, which contains genes for chloramphenicol resistance and T7 lysozyme (20), may be included in the expression strain. Since the presence of T7 lysozyme inhibits the action of T7 RNA polymerase, this can serve to prevent pre-induction expression of the recombinant somatotropin binding protein, as well as potentiating lysis of the induced bacteria.

The strain JM 109 (DE3)/pET 7-6 m is grown overnight in M9 medium containing ampicillin (100 μg/ml), 1% casamino acids and 20 g/l glucose. This is introduced into a fermentor, grown at 37° C. to an $OD_{600}$ of about 15 and induced by adding 0.4 mM IPTG to the medium. After 2.5 hours, cells are harvested and frozen. Cells are resuspended in water, homogenized with a polytron or other cell disruption method (if pLysS is not used) and sonicated to disrupt genomic DNA. The recombinant product, in the form of inclusion bodies, is pelleted, washed, solubilized at high pH and purified by ultrafiltration with hollow fiber filters (Amicon) and chromatography on ion exchange, hydrophobic interaction or affinity columns.

A clone from hybridoma GHBP-4 is selected and designated GHBP-4.3 (ATCC HB 10310) as exemplary for further study. GHBP-4.3 is injected intraperitoneally into Balb/C mice primed with pristane for the production of antibody-containing ascites.

EXAMPLE 4

Purification of Antibody

Ascites are collected from the peritoneal cavities of mice and Ig is purified by 50% ammonium sulfate precipitation technique. Alternatively, samples are diluted to 50% with binding buffer (3M NaCl, 1.5M glycine, pH 8.9) and loaded to a preparative Protein A Superose HR 16/5 column on a fast protein liquid chromatography (FPLC) system (Pharmacia, Inc., Piscataway, N.J.). Non-Ig fraction is eluted from the column with the binding buffer and the bound Ig is subsequently collected by rinsing the column with 0.1M citric acid, pH 3. It is immediately neutralized to pH 7–8 with 2M Tris buffer, pH 8.2. Antibody prepared by both procedures is extensively dialyzed against PBS, concentrated by ultrafiltration (Amicon, Danvers, Mass.), aliquoted, and finally stored at −20° C. until use.

EXAMPLE 5

Solid Phase ELISA

Antigens are dissolved in PBS and 1 μg in 100 μl are added to each well of a 96-well flat bottom polystyrene plate. After being incubated for one hour, the plate is washed 3 times with PBS containing 0.05% Tween-20 by an automatic plate washer (Dynatech Wash II, Chantilly, Va.). Each well is dispensed with 200 μl of 2% BSA (Sigma) and the plate is incubated for another hour. Test samples are added to the wells, incubated for 30 minutes, washed 6 times with PBS, and added with 100 μl of alkaline phosphatase-conjugated goat anti-mouse IgG F(ab')$_2$ (Zymed Laboratories, South San Francisco, Calif.). The plate is again washed after a 30 minute incubation and 100 μl of p-nitrophenyl phosphate (lmg/ml, Sigma) in 0.1M diethanolamine, pH 10.3, is added as substrate for color development. Finally, the colorimetric response is recorded as optical density (OD) by an ELISA plate reader at a wavelength of 405 nm. Incubation procedure is always performed at 37° C.

EXAMPLE 6

Western Blot Assay for Specific Binding of Monoclonal Antibodies to Somatotropin Binding Protein The E. coli bacteria described in Example 3 or the purified somatotropin binding protein from these bacteria are used for Western blot assay to determine the specific interaction of the monoclonals with somatotropin binding protein. The rat somatotropin binding protein expressed in these bacteria contains 262 amino acids and an apparent molecular weight of 30 Kd as judged by SDS-PAGE. The E. coli lysate containing somatotropin binding protein is boiled in SDS-PAGE sample buffer containing 40 mM Tris pH 7.4, 5 mM EDTA, 3% SDS, 1 μl 2-mercaptoethanol and electrophoresed on 15% polyacrylamide. The gel is then electroblotted on Immobilon-P filter paper (Millipore). The blot is probed with GHBP-4.3 monoclonal antibody raised against the 17 amino acids of the carboxy-terminal end of the binding protein. As shown in FIG. 1, the monoclonal antibody specifically recognizes the somatotropin binding protein in the E. coli extract (Lane 2). The monoclonal antibody does not interact with any protein of E. coli which contains an expression plasmid in which the somatotropin binding protein sequence is in reverse orientation (such a strain is unable to express the somatotropin binding protein) (Lane 1).

EXAMPLE 7

Identification of Somatotropin Binding Protein by GHBP-4.3 Monoclonal Antibody

GHBP-4.3 monoclonal antibody is used to identify the rat circulating somatotropin binding protein. For this, rat plasma is prepared by drawing 5 ml of rat blood directly in 1 ml 0.5M EDTA. 1 μl of plasma is denatured in 20 μl sample buffer (containing 50 mM Tris pH 7.4, 5 mM EDTA, 3% SDS, 1 μl 2-mercaptoethanol) and heated for three minutes (100° C.). The plasma sample is then electrophoresed on 15% discontinuous polyacrylamide gel and the proteins separated on the gel are electroblotted on Immobilon-P filter paper. The blot is incubated with GHBP-4.3 monoclonal antibody (50 μl ascites in 10 ml of 10 mM Tris pH 7.4, 150 mM NaCl, 5% nonfat milk and 0.05% sodium azide) for two hours at room temperature, washed in 10 mM Tris, 150 mM NaCl, and exposed to alkaline phosphatase labelled anti-mouse antibody for another two hours at room temperature. The blot is washed again and developed for alkaline phosphatase reaction with its substrate nitroblue tetrazolium chloride (NBT) plus 5-bromo-4-chloro-3-indolylphosphate p-toluidine salt (BCIP) in 100 mM NaHCO$_3$ plus 1 mM MgCl$_2$. As shown in FIG. 2 (Lane 1), the antibody specifically reacts with a protein with a molecular weight of 48 Kd. The size of this protein is in the range expected for somatotropin binding protein considering that its core protein (which contains no post-translational modifications) has a calculated molecular weight of 30 Kd and that it contains carbohydrate chains as its post-translational modification. In contrast, the molecular weight of the somatotropin receptor is approximately 120 Kd (9).

The cross-reactivity of GHBP-4.3 monoclonal antibody with the somatotropin binding protein of other animals is analyzed by subjecting the EDTA-treated plasma of various animals to SDS-PAGE and Western blotting. The blot is incubated with the monoclonal antibody and later with goat anti-mouse antibody labelled with alkaline phosphatase as described above. The result of this experiment is shown in FIG. 2. The monoclonal antibody reacts with rat, mouse and pig somatotropin binding protein, but not with the cow, sheep, chicken and human binding protein. This experiment also reveals that the mouse somatotropin binding protein has an apparent molecular weight of 48 Kd and the pig somatotropin binding protein has an apparent molecular weight of 60 Kd.

In order to show that the GHBP-4.3 monoclonal antibody does not bind to the somatotropin receptor, the cell lysate of clone 9 cells, a rat hepatoma cell line which has been shown to contain the somatotropin receptor (American Type Culture Collection, Rockville, Md.), is also subjected to SDS-PAGE and Western blotting. The monoclonal antibody does not cross-react with the somatotropin receptor.

EXAMPLE 8

Immunoprecipitation of Somatotropin Binding Protein with GHBP-4.3 Monoclonal Antibody Fifty μl of EDTA-treated rat plasma are incubated overnight at 4° C. with 1 ml of 25 mM Tris buffer containing 150 mM NaCl, 5 m/M EDTA, 0.5% NP-40 (a detergent), 3% BSA, and 0.3 μCi of $^{125}$I-bovine somatotropin (5 ng) pH 7.5. GHBP-4.3 antibody is added (5 μg) and the whole complex is precipitated with formalin-fixed staph A bacteria for an additional hour at room temperature. The complex is washed three times in 0.5% NP-40, 25 mM Tris pH 7.5, 150 mM NaCl and 5 mM EDTA and then dissociated by heating in 2X SDS-PAGE sample buffer for three minutes. The sample is electrophoresed on 15% SDS-PAGE, the gel is fixed, dried, and finally exposed to x-ray film for autoradiography.

Figure 3:
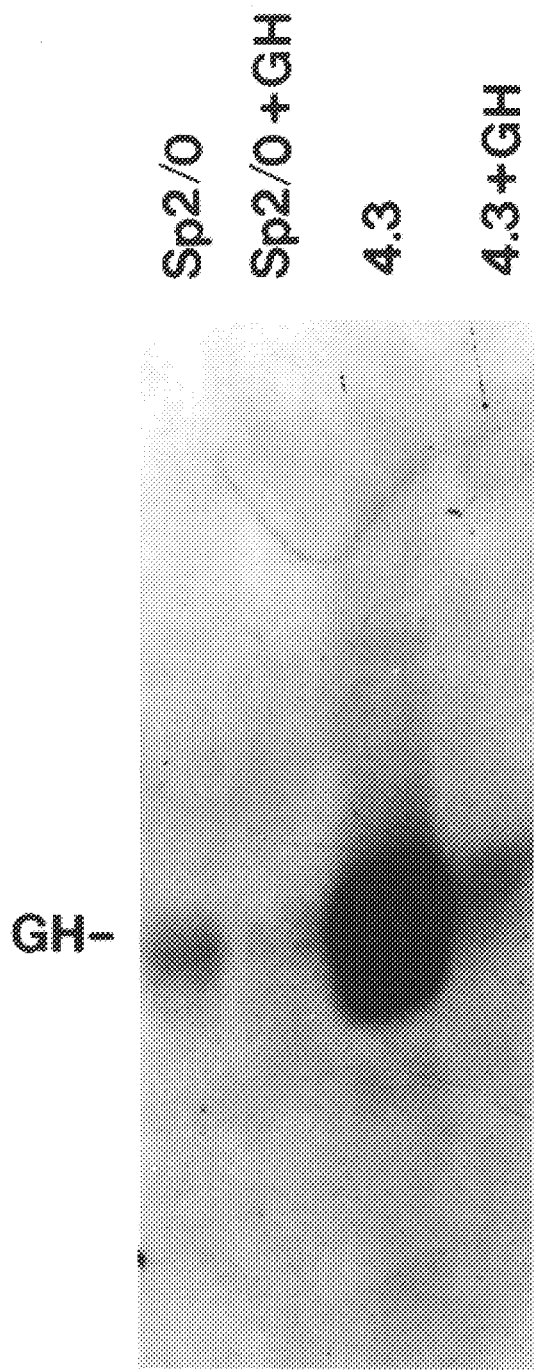
FIG. 3 depicts the specific binding of GHBP-4.3 monoclonal antibody to a somatotropin binding protein/somatotropin complex. The complex of rat somatotropin binding protein and $^{125}$I-somatotropin was immunoprecipitated with GHBP-4.3 monoclonal antibody and formalin-fixed Staph A. The complex was dissociated in sample buffer and electrophoresed on 15% polyacrylamide gel. The gel was then fixed, dried and autoradiographed. The autoradiogram shows the radioactive somatotropin which was precipitated. The Figure shows the immunoprecipitation of the somatotropin binding protein/somatotropin complex with SP2/0 antibody (Lane 1), SP2/0 antibody and excess unlabelled somatotropin (Lane 2), GHBP-4.3 monoclonal antibody (Lane 3) and GHBP-4.3 monoclonal antibody and excess unlabelled somatotropin (Lane 4). In this Figure, somatotropin is indicated by "GH".

As shown in FIG. 3, after immunoprecipitation of the radioactive complex with GHBP-4.3 monoclonal antibody, a protein band of 20 Kd corresponding to the $^{125}$I-labelled somatotropin is observed, indicating that the antibody specifically recognizes somatotropin binding protein which binds to $^{125}$I-somatotropin (Lane 3). Antibodies derived from SP2/0 parental line and normal mice are used as controls and no protein band or very faint band is demonstrated (Lane 2). Addition of excess unlabelled somatotropin causes the disappearance of the radioactive somatotropin, indicating that the immunoprecipitation of somatotropin is dependent on the presence of somatotropin binding protein. Thus, GHBP-4.3 monoclonal antibody specifically binds to somatotropin binding protein after forming a complex with somatotropin. Addition of the monoclonal antibody at the same time as the radiolabelled somatotropin does not alter the pattern of immunoprecipitation, suggesting that this antibody does not interfere with the binding site of somatotropin to the binding protein.

EXAMPLE 9

Effect of GHBP-4.3 Monoclonal Antibody on Growth

To investigate the effect of the monoclonal antibody GHBP-4.3 in vivo, passive immunization is used. The antibody is injected directly in young mice and their growth is followed by measuring their weight gain. Three groups of 10 mice/group are injected with:

1. 200 µl ascites fluid containing 1 mg of GHBP-4.3 monoclonal antibody per mouse.
2. 200 µl ascites fluid containing normal mouse polyclonal antibodies per mouse (as control).
3. Untreated control.

The data on increase in average weight gain per group are presented in Table II:

TABLE II

| Day | Average Weight Gain (in grams) | | |
| --- | --- | --- | --- |
| | GHBP-4.3 Monoclonal Antibody Treated Mice | Treated Control Mice | Untreated Control Mice |
| 3 | 2.4 | 1.31 | 1.6 |
| 5 | 3.78 | 2.77 | 2.65 |
| 8 | 5.7 | 5.52 | 4.45 |
| 11 | 7.3 | 7.42 | 6.08 |
| 14 | 8.7 | 8.52 | 7.45 |
| Starting weight Day 0 (average) | 10.3 | 9.68 | 10.55 |

The data indicate that, at the end of 14 days, the mice treated with GHBP-4.3 monoclonal antibody have a larger average weight gain than the mice which are treated with normal mouse antibody or are not treated. A comparison between the mice treated with GHBP-4.3 monoclonal antibody and the untreated mice is shown in FIG. 4A.

In a similar experiment shown in FIG. 4B, a combination of GHBP-4.3 monoclonal antibody and somatotropin is used to investigate the effect of the antibody on the growth rate. Groups of four mice each are treated with 100 µg GHBP-4.3 monoclonal antibody plus 10 µg mouse somatotropin, 10 µg mouse somatotropin alone or 100 µg of control mouse IgG per mouse. As shown in FIG. 4B, the mice which receive GHBP-4.3 monoclonal antibody plus somatotropin gain weight at a faster rate than control mice or the mice treated with somatotropin alone.

These experiments in Examples 8 and 9 strongly suggest that the manipulation of somatotropin binding protein has a profound influence on the rate of weight gain.

BIBLIOGRAPHY

1. Hughes, J. P. and Friesen, H. G., *Ann. Rev. Physiol.*, 47, 469–482 (1985).
2. Ymer, S. I. and Herington, A. C., *Mol. Cell. Endocrinol.*, 41, 153–161 (1985).
3. Baumann, G., et al., *J. Clin. Endo. Metab.*, 62, 134–141 (1986).
4. Herington, A. C., et al., *J. Clin. Invest.*, 77, 1817–1823 (1986).
5. Eshet, R., et al., *Israel J. Med. Sci.*, 20, 8–13 (1985).
6. Barnard, R. and Waters, M. J., *Biochem. J.*, 237, 885–892 (1986).
7. Baumann, G., et al., *J. Clin. Endo. Metab.*, 65, 814–816 (1987).
8. Daughaday, W. H. and Trivedi, B., *Proc. Natl. Acad. Sci.*, 84, 4636–4640 (1987).
9. Leung, D. W., et al., *Nature*, 330, 537–543 (1987).
10. Baumann, G. and Shaw, M. A., *Biochem. Biophys. Res. Commun.*, 152, 573–578 (1988).
11. Spencer, S. A., et al., *J. Biol, Chem.*, 263, 7862–7867 (1988).
12. U.S. Pat. No. 4,857,637.
13. Trivedi, B. and Daughaday, W. H., *Endocrinology*, 123, 2201–2206 (1988).
14. Baumbach, W. R., et al., *Genes & Development*, 3, 1195–1205 (1989).
15. Smith, W. C., et al., *Mol. Endo.*, 3, 984–990 (1989).
16. Dunn, J. J. and Studier, F. W., *J. Mol. Biol.*, 166, 477–535 (1983).
17. Rosenberg, A. H., et al., *Gene*, 56, 125–135 (1987).
18. Mathews, L. S., et al., *J. Biol. Chem.*, 264, 9905–9910 (1989).
19. Studier, F. W. and Moffatt, B. A., *J. Mol. Biol.*, 189, 113–130 (1986).
20. Moffatt, B. A. and Studier, F. W., *Cell*, 49, 221–227 (1987).

We claim:

1. A method for enhancing growth in an animal species which comprises administering to said animal species an effective growth enhancing amount, as characterized by an increase in weight gain of said animal species, of a monoclonal antibody, wherein said monoclonal antibody binds to the somatotropin binding protein in said animal species, but which does not bind to the corresponding somatotropin receptor in said species, and wherein said monoclonal antibody binds to a unique carboxyl terminal segment of said somatotropin binding protein which is generated by an alternative splicing mechanism and which is absent in said somatotropin receptor.

2. The method of claim 1, wherein the monoclonal antibody is GHBP-4.3 monoclonal antibody.

3. The method of claim 1, wherein the animal species is a pig, a rat or a mouse.

4. A method for potentiating the effect of somatotropin in an animal species, which comprises administering to said animal an effective growth enhancing amount, as characterized by an increase in weight gain of said animal species, of somatotropin and an effective growth enhancing amount, as characterized by an increase in weight gain of said animal species, of a monoclonal antibody, wherein said monoclonal antibody binds to the somatotropin binding protein in said animal species, but which does not bind to the corresponding somatotropin receptor in said species, and wherein said monoclonal antibody binds to a unique carboxyl terminal segment of said somatotropin binding protein which is generated by an alternative splicing mechanism and which is absent in said somatotropin receptor.

5. The method of claim 4, wherein the monoclonal antibody is GHBP-4.3 monoclonal antibody.

6. The method of claim 4, wherein the animal species is a pig, a rat or a mouse.

7. A pharmaceutical composition comprising an effective growth enhancing amount, as characterized by an increase in weight gain of an animal species, of a monoclonal antibody which binds to the somatotropin binding protein in said animal species, but which does not bind to the corresponding somatotropin receptor in said species and a pharmaceutically acceptable carrier, wherein the monoclonal antibody binds to a unique carboxyl terminal segment of said somatotropin binding protein which is generated by an alternative splicing mechanism and which is absent in said somatotropin receptor.

8. The pharmaceutical composition of claim 7 which further comprises an effective growth enhancing amount, as characterized by an increase in weight gain of said animal species, of somatotropin.

* * * * *